United States Patent [19]

Bruchmann et al.

[11] Patent Number: 5,436,336
[45] Date of Patent: Jul. 25, 1995

[54] PREPARATION OF ISOCYANURATE- AND/OR URETDIONE-CONTAINING POLYSIOCYANATES HAVING A REDUCED COLOR INDEX AND IMPROVED SHELF LIFE, AND PRODUCTS PREPARED BY THIS METHOD

[75] Inventors: Bernd Bruchmann, Ludwigshafen; Stefan Wolff, Limburgerhof; Konrad Stiefenhoefer, Ebertsheim, all of Germany

[73] Assignee: BASF Aktiengesellschaft, Ludwigshafen, Germany

[21] Appl. No.: 259,105

[22] Filed: Jun. 13, 1994

[30] Foreign Application Priority Data

Jun. 23, 1993 [DE] Germany ............... 43 20 821.5

[51] Int. Cl.⁶ ........................................... C07D 251/32

[52] U.S. Cl. .................... 544/193; 548/317.1; 548/319.1

[58] Field of Search .............. 544/193; 548/317.1, 548/319.1

[56] References Cited

U.S. PATENT DOCUMENTS 4,994,541 2/1991 Dell et al. .
5,237,058 8/1993 Laas et al. ............... 540/202

Primary Examiner—José G. Dees
Assistant Examiner—Samuel Barts
Attorney, Agent, or Firm—Dennis V. Carmen

[57] ABSTRACT

Isocyanurate- and/or uretidone-containing polyisocyanates having a reduced color index and improved shelf life are prepared by conventional catalytic oligomerization of aliphatic and/or cycloaliphatic diisocyanates and treatment of the oligomerization products with peroxycarboxylic acids.

18 Claims, No Drawings

PREPARATION OF ISOCYANURATE- AND/OR URETDIONE-CONTAINING POLYSIOCYANATES HAVING A REDUCED COLOR INDEX AND IMPROVED SHELF LIFE, AND PRODUCTS PREPARED BY THIS METHOD

The present invention relates to a process for the preparation of isocyanurate- and uretdione-containing polyisocyanate mixtures having a reduced color index by catalytic oligomerization of aliphatic and/or cycloaliphatic diisocyanates and subsequent removal of the unconverted diisocyanates. The present invention furthermore relates to the products prepared by this process.

For high quality one-component and two-component polyurethane finishes having high light stability and weather stability, the isocyanate components used are in particular isocyanurate- and uretdione-containing polyisocyanate mixtures.

These products are preferably prepared by catalytic oligomerization of aliphatic and/or cycloaliphatic diisocyanates, eg. 1-isocyanato-3,3,5-trimethyl-5-isocyanatomethylcyclohexane (IPDI) or 1,6-diisocyanatohexane (HDI).

The catalysts used may be, for example, hydroxides or organic salts of weak acids having tetraalkylammonium groups, hydroxides or organic salts of weak acids having hydroxyalkylammonium groups, alkali metal salts or tin, zinc or lead salts of alkanecarboxylic acids.

The aliphatic and/or cycloaliphatic diisocyanates are allowed to react in the presence of the catalyst, with or without the use of solvents and/or assistants, until the desired conversion has been reached. Thereafter, the reaction is stopped by deactivating the catalyst and the excess monomeric diisocyanate is distilled off. Depending on the catalyst type used and on the reaction temperature, polyisocyanates having different contents of isocyanurate and uretdione groups are obtained.

The products thus prepared are generally clear products which, however, depending on the catalyst the diisocyanate quality, the reaction temperature and the reaction procedure, are more or less strongly yellow.

However, products having a very low color index are desirable for the production of high quality polyurethane finishes. The prior art discloses a number of methods for reducing the color index of such products.

For example, DE-A-38 06 276 proposes reducing the carbon dioxide content of the HDI used as a monomer to less than 20 ppm before the oligomerization by degassing under reduced pressure and subsequently blowing nitrogen through the HDI, and using a quaternary ammonium hydroxide as the oligomerization catalyst. The process step of carbon dioxide removal is, however, technically very complicated.

EP-A-0 339 396 proposes the use of a quaternary ammonium fluoride as a trimerization catalyst. In this process, a higher carbon dioxide content can be tolerated but the proposed catalyst must be chemically deactivated. The resulting compounds remain in the product and may give rise to problems with performance characteristics during further processing. A further possibility for the preparation of isocyanurate-containing polyisocyanates having a lower color index is to add polyesterdiols to the starting diisocyanate, as proposed in EP-A-0 336 205. This makes it possible to reduce the amount of catalyst used. However, the resulting products still have a relatively strong color.

In EP-A-0 377 177, the aliphatic diisocyanate is oligomerized in the presence of a phosphine as a catalyst, and the unconverted diisocyanate is partly distilled off after the oligomerization has been stopped and partly converted into urethane by the addition of alcohol. The reaction product is then treated with peroxides. Although the peroxide treatment results in a reduction in the color index of the oligomerization product, the use of peroxides often gives rise to problems. For example, peroxides are technically difficult to handle. Peroxides which are safer to handle are generally available in solution, dibutyl phthalate, frequently used as a solvent, then leading to problems with the performance characteristics during production of the finish.

A further substantial disadvantage of the prior art process is that the shelf life of the products thus obtained is insufficient. The color properties deteriorate and in particular there is a substantial increase in the viscosity.

It is an object of the present invention to provide a simple process for the preparation of isocyanurate- and/or uretdione-containing polyisocyanates having a reduced color index, which process avoids the disadvantages of the prior art and in particular leads to products having an improved shelf life.

We have found that this object is surprisingly achieved, according to the invention, by a process for the preparation of isocyanurate- and/or uretdione-containing polyisocyanates by conventional catalytic oligomerization of aliphatic and/or cycloaliphatic diisocyanates, in which the oligomerization products are treated with peroxycarboxylic acids to lighten the color.

The present invention furthermore relates to the isocyanurate- and/or uretdione-containing polyisocyanates having a reduced color index and prepared by this process.

In a particularly advantageous embodiment of the invention, when basic, in particular amine, oligomerization catalysts are used, the peroxycarboxylic acids are added to deactivate the catalyst when the desired degree of oligomerization has been reached, and the oligomerization product is then worked up in the conventional manner used in the prior art, by removal of monomers, generally under greatly reduced pressure by means of a thin-film evaporator. A special process step for lightening the oligomerization products is then no longer required.

The oligomerization of the aliphatic and/or the cycloaliphatic diisocyanates is carried out by the method usual in the prior art.

The starting diisocyanates used are aliphatic and/or cycloaliphatic diisocyanates, eg. 1,4-diisocyanatohexane, 1,6-diisocyanatohexane (HDI), 1,12-diisocyanatododecane, 1-isocyanato-3,3,5-trimethyl-5-isocyanatomethylcyclohexane (IPDI), 4,4'-diisocyanatodicyclohexylmethane, 1,5-diisocyanato-2,2-dimethylpentane, 1,5-diisocyanato-2-ethyl-2-propylpentane, 1,6-diisocyanato-2,4,4-trimethylhexane and 1,5-diisocyanato-2-methylpentane, in particular HDI.

The oligomerization of the diisocyanates is preferably carried out at from 0° to 100° C. by passing through inert gas, preferably nitrogen. The reaction rate is too low at lower temperatures, while the level of secondary reactions is greater at higher temperatures.

The catalysts used may be any catalysts suitable for the oligomerization of aliphatic and/or cycloaliphatic diisocyanates, for example hydroxides or organic salts of weak acids having tetraalkylammonium groups, hydroxides or organic salts of weak acids having hydroxyalkylammonium groups, alkali metal salts or tin, zinc or lead salts of alkanecarboxylic acids. The catalysts are usually used in an amount of from 0.05 to 2% by weight, based on the diisocyanate.

To reduce the amount of catalyst, it is possible to add a small amount, up to about 1% by weight, based on the diisocyanate, of a diol, in particular a polyesterdiol, to the diisocyanates in a manner known per se, prior to oligomerization.

Thereafter, the diisocyanate is brought to the reaction temperature with stirring and the catalyst is slowly added. To improve the handling, the catalyst may be dissolved in a solvent. For example, alcohols, in particular diols, ketones, ethers and esters are suitable for this purpose.

After the desired conversion has been reached, the reaction is stopped by deactivation of the catalyst, for example by the addition of a catalyst poison or by thermal decomposition of the catalyst. The reaction mixture is then freed from the monomeric diisocyanates in a suitable manner known per se, for example by distillation, eg. by means of a thin-film evaporator.

A particularly advantageous and therefore preferred embodiment of the invention comprises, as stated above, using the peroxycarboxylic acids as neutralizing agents for the basic oligomerization catalysts employed. The novel peroxycarboxylic acids are added to the reaction mixture in an amount of from 10 to 10,000 ppm, preferably from 50 to 1,000 ppm, based on the reaction mixture, when the desired degree of oligomerization has been reached, in order to deactivate the catalyst and hence to stop the reaction. The peroxycarboxylic acids may also be used together with conventional neutralizing agents. The reaction mixture is then freed from the monomeric diisocyanates in a suitable manner known per se, for example by distillation, eg. by means of a thin-film evaporator.

For the purposes of the present invention, it is, however, also possible to deactivate the catalyst in another suitable manner, for example by means of catalyst poisons or by thermal decomposition, when the desired degree of oligomerization has been reached. The reaction mixture is then freed from the monomeric diisocyanates in the manner described. The novel peroxycarboxylic acids are added in an amount of from 10 to 10,000 ppm, preferably from 50 to 1,000 ppm, based on the amount of diisocyanate, to the solution worked up in this manner.

The peroxycarboxylic acids used may be aromatic, aliphatic, cycloaliphatic, unsubstituted or substituted peroxycarboxylic acids. It is also possible to use acidic salts of these peroxycarboxylic acids.

Examples of peroxycarboxylic acids are peracetic acid, peroxymaleic acid, tert-butyl peroxymaleic acid, perbenzoic acid, p-nitrobenzoic acid, peroxyphthalic acid and in particular 3-chloroperbenzoic acid. Ammonium or magnesium salts are used in particular as acidic salts of the peroxycarboxylic acids.

The novel process for the preparation of isocyanurate- and/or uretdione-containing polyisocyanates leads to products having low color indices. The color indices are below 50 HAZEN but generally below 30 HAZEN. However, the particular advantage of the products prepared according to the invention is their very good shelf life. Even after a storage time of 6 months under a nitrogen atmosphere, there was no change in the color, and furthermore the increase in the viscosity of these products was corresponding smaller than in the case of those which had been prepared by the prior art processes.

An additional advantageous effect occurred in the neutralization of the oligomerization catalyst with peroxycarboxylic acids. Here, the monomeric diisocyanate distilled off after the oligomerization of the aliphatic and/or cycloaliphatic diisocyanates did not exhibit the disadvantages otherwise frequently encountered in the case of the corresponding-products of the prior art processes.

While, in the neutralization of the oligomerization catalyst with the alkyl phosphates generally used in the prior art processes, the reactivity of the recycled diisocyanate monomers was substantially lower than that of fresh diisocyanate and it is therefore necessary to use a larger amount of catalyst, the monomeric diisocyanate recycled in the neutralization of the oligomerization catalyst with peroxycarboxylic acids exhibited no such behavior and could be readily oligomerized under the conventional process conditions and with the use of the usual amount of catalyst.

In the thermal decomposition of the oligomerization product, likewise known from the prior art, the recycled monomeric diisocyanate generally exhibits no differences in reactivity compared with fresh diisocyanate, but gelling of these products frequently occurs. Furthermore, such behavior was not observed in the case of the monomeric diisocyanates obtained by the novel process.

The novel products are generally used as isocyanate components in polyurethane one-component and two-component finishes.

The Examples which follow illustrate the invention.

EXAMPLE 1 (COMPARISON)

500 g of 1,6-diisocyanatohexane (HDI) were heated to 80° C. under a nitrogen blanket, and 400 ppm of N,N,N-trimethyl-N-(2-hydroxypropyl)-ammonium 2-ethylhexanoate, dissolved in 2 ml of methyl ethyl ketone (MEK), were added while stirring.

When the NCO content of the reaction mixture was 43% by weight, 2 mol equivalents, based on the amount of catalyst, of dibutyl phosphate were added and stirring was continued for 1 hour at 80° C. Unconverted HDI was then stripped off under greatly reduced pressure by means of a thin-film evaporator.

The color index of the oligomerized HDI was 78 HAZEN. 400 ppm of N,N,N-trimethyl-N-(2-hydroxypropyl)ammonium 2-ethylhexanoate were then added, while stirring, to 250 g of the monomeric HDI stripped off. No decrease in the NCO content was observed.

EXAMPLE 2 (COMPARISON)

The procedure was as in Example 1, except that the reaction mixture was heated for 15 minutes at 110° C. to deactivate the catalyst.

The monomeric HDI stripped off had a normal reactivity but gelled on standing in a closed vessel under nitrogen at 5° C.

EXAMPLE 3

The procedure was as in Example 1, except that 2 mol equivalents, based on the catalyst, of 3-chloro-perbenzoic acid were used to neutralize the catalyst.

The color index of the oligomerization product was 25 HAZEN. 400 ppm of N,N,N-trimethyl-N-(2-hydroxypropyl)-ammonium 2-ethylhexanoate, dissolved in 2 ml of MEK, were added at 80° C. to 200 g of the monomeric HDI stripped off.

The decrease in the NCO content was the same as for fresh monomeric HDI. When an NCO content of 43% by weight, based on the reaction mixture, had been reached, the catalyst was neutralized by adding 2 mol equivalents of 2-chloroperbenzoic acid. The oligomerization product had a color index of 20 HAZEN. 50 g of the monomeric HDI stripped off were stored at 5° C. for 4 weeks under nitrogen in a closed vessel. No gel formation occurred.

EXAMPLE 4

The procedure was as in Example 1, except that 2 mol equivalents of 4-nitroperbenzoic acid were used to neutralize the catalyst. The color index of the oligomerization product was 27 HAZEN.

EXAMPLE 5

The procedure was as in Example 1, except that 2 mol equivalents of magnesium monoperoxyphthalate were used to neutralize the catalyst. The color index of the oligomerization product was 50 HAZEN.

EXAMPLE 6 (COMPARISON)

Uretdione- and isocyanurate-containing HDI prepared according to Example 2, was stored under nitrogen for 6 months at 50° C. after the monomeric HDI had been separated off. The viscosity increased during this period from 2,460 mPa.s at 25° C. to 5,870 mPa.s at 25° C. The color index of the product remained constant at 30 HAZEN.

EXAMPLE 7

300 ppm of 3-chloroperbenzoic acid were added to the uretdione- and isocyanurate-containing HDI used in Example 6, after the monomeric HDI had been separated off. The product treated in this manner was stored at 50° C. under nitrogen for 6 months. The viscosity of the product increased from 2,460 mPa.s at 25° C. to 2,920mPa.s at 25° C. and the color index remained constant at 10 HAZEN.

The HAZEN color index was determined according to DIN 53,995.

We claim:

1. A process for the preparation of an isocyanurate- or uretdione-containing polyisocyanate having a reduced color index and improved shelf life comprising oligomerization of aliphatic or cycloaliphatic diisocyanates using oligomerization catalysts comprising hydroxides or organic salts of acids having tetraalkylammonium or hydroxyalylammonium groups, alkali metal salts, or tin, zinc, or lead salts of alkanecarboxylic acids, and subsequently neutralizing said oligomerization catalyst with a peroxycarboxylic acid.

2. A process as claimed in claim 1, wherein the starting diisocyanate is 1,6-diisocyanatohexane.

3. A process as claimed in claim 1, wherein the peroxycarboxylic acid is used for deactivating the oligomerization catalyst.

4. A process as claimed in claim 1, wherein unconverted monomeric diisocyanates are removed from the oligomerization product, and the peroxycarboxylic acid is added to the oligomerization product after the removal of the unconverted monomeric diisocyanates.

5. A process as claimed in claim 1, wherein the peroxycarboxylic acid is used in an amount of from 10 to 10,000 ppm, based on the diisocyanate used.

6. A process as claimed in claim 1, wherein the peroxycarboxylic acid is used in an amount of from 50 to 1,000 ppm, based on the diisocyanate used.

7. The process of claim 1, comprising oligomerizing a reaction mixture of catalyst and aliphatic or cycloaliphatic diisocyanates, adding the peroxycarboxylic acid to the reaction mixture when the desired degree of oligomerization is obtained, and subsequently removing unreacted monomeric diisocyanates from the reaction mixture.

8. The process of claim 7, wherein from 10 to 10,000 ppm of peroxycarboxylic acid are added, based on the weight of the reaction mixture.

9. The process of claim 8, wherein the amount of peroxycarboxylic acid is from 50 to 1,000 ppm.

10. The process of claim 1, comprising oligomerizing a reaction mixture of catalyst and aliphatic or cycloaliphatic diisocyanates to the desired degree of oligomerization, removing unreacted monomeric diisocyanates, and subsequently adding peroxycarboxylic acid.

11. The process of claim 10, wherein the amount of peroxycarboxylic acid added is from 10 to 10,000 ppm based on the amount of diisocyanates used.

12. The process of claim 11, wherein the amount of peroxycarboxylic acid is from 50 to 1,000 ppm.

13. The process of claim 1, wherein the peroxycarboxylic acids comprise peracetic acid, peroxymaleic acid, tert-butyl peroxymaleic acid, perbenzoic acid, p-nitrobenzoic acid, peroxyphthalic acid, 3-chloroperbenzoic acid, or salts thereof.

14. The process of claim 13, wherein the salts comprise magnesium or ammonium salts of the acids.

15. The process of claim 13, wherein the acid comprises 3-chloroperbenzoic acid.

16. The process of claim 1, wherein the isocyanurate- or uretdione-containing polyisocyanate has a color index below 50 HAZEN.

17. The process of claim 16, wherein the color index is below 30 HAZEN.

18. The process of claim 1, wherein the isocyanurate- or uretdione-containing polyisocyanate does not change color at six months of storage under a nitrogen atmosphere.

* * * * *